United States Patent [19]

Wolinsky

[11] Patent Number: 4,824,436
[45] Date of Patent: Apr. 25, 1989

[54] METHOD FOR THE PREVENTION OF RESTENOSIS

[76] Inventor: Harvey Wolinsky, 175 Riverside Dr., New York, N.Y. 10024

[21] Appl. No.: 42,569

[22] Filed: Apr. 21, 1987

[51] Int. Cl.⁴ .............................................. A61M 5/00
[52] U.S. Cl. ...................................... 604/53; 604/101
[58] Field of Search ................................... 604/52-53, 604/101, 102; 128/344, 348.1

[56] References Cited

U.S. PATENT DOCUMENTS

| | | | |
|---|---|---|---|
| 4,299,226 | 11/1981 | Banka | 604/53 X |
| 4,423,725 | 1/1984 | Baran et al. | 604/101 X |
| 4,445,892 | 5/1984 | Hussein | 604/101 |
| 4,573,966 | 3/1986 | Weikl et al. | 604/53 |

Primary Examiner—Dalton L. Truluck
Attorney, Agent, or Firm—Wyatt, Gerber, Shoup and Badie

[57] ABSTRACT

Process for local administration of heparin or other agents to inhibit arterial smooth muscle cell proliferation utilizing a catheter.

6 Claims, 1 Drawing Sheet

METHOD FOR THE PREVENTION OF RESTENOSIS

RELATED APPLICATION

This application is a continuation in part application of copending application Ser. No. 721,386 filed Apr. 9, 1985, now abandoned.

BACKGROUND OF THE INVENTION

Recently an alternative approach to coronary bypass surgery has been developed. In this non-operative procedure for the improvement of blood flow in patients with coronary artery disease, a catheter with an inflatable balloon at the distal end is inserted into the femoral artery or by brachial cutdown, and is positioned by fluoroscopic control at the appropriate coronary ostium. The process is known as percutaneous transluminal coronary angioplasty (PTCA).

The balloon at the distal end of the catheter has a predetermined maximum diameter. It is filled with a radio opaque dye to permit visualization. Alternatively, the balloon itself may be radio opaque. When the balloon is positioned in the stenosis it is inflated at pressures of from 2 to 11 atmospheres for from 15 to 60 seconds and then deflated. The inflation cycle may be repeated several times to achieve satisfactory results. Normally the luminal diameter of the stenotic vessel increases at least 20% as a result of the treatment.

Angioplasty is not limited to the cardiac vasculature. It has been employed for treatment of single, large atherosclerotic lesions of the renal, iliac and even vertebral arteries. The effect of the expanded balloon is to literally blow open the stenotic zone. Disruption of the wall is marked, including fracture of the calcium in the lesion, tearing of the plaque itself and extravasation of plaque lipid and gruel into the adjacent vessel wall.

The clinical results of angioplasty include endothelial denudation, vascular wall damage, and rupture of the tunica intima vasorum. These injuries have been found to result in many cases in unregulated proliferation of the arterial smooth muscle cells (SMC) with a resulting restenosis. A recent study by Levine et al (The American Journal of Cardiology, Volume 55, pages 673 to 676, March 1985) has shown that restenosis may be expected to occur in as many as 40% of patients that have undergone angioplasty. Often the only practical treatment for restenosis is to repeat the treatment. This may cause further damage to the cell wall and the need for subsequent repetition of the angioplasty procedure.

Heparin is a mucopolysaccharide composed of amino sugar and uronic acid residues which is obtained from beef, porcine, sheep, whale and other mammalian tissue by extraction with a solution of potassium acetate, alkaline ammonium sulfate and the like. Commercial heparin preparations are now widely available from a number of pharmaceutical companies. Heparin preparations are clinically utilized principally as anticoagulants.

Recently it has become known that in addition to its anticoagulant activities, heparin is a powerful inhibitor of arterial smooth muscle proliferation. See, for example, Guyton et al. Circulation Research Volume 46, Number 5 pages 625 to 633, 1980 and Hoover et al. Circulation Research Volume 47, Number 4, pages 578 to 583, 1980.

My co-pending U.S. patent application Ser. No. 364,408, filed Apr. 2, 1982 describes and claims catheters which can be used to insert a solubilizing agent into an artery to dissolve plaque thereby relieving arterial constrictions. The disclosure of this application is incorporated herein by reference.

This invention will be better understood by reference to the figures. In the drawing.

Figure 1:
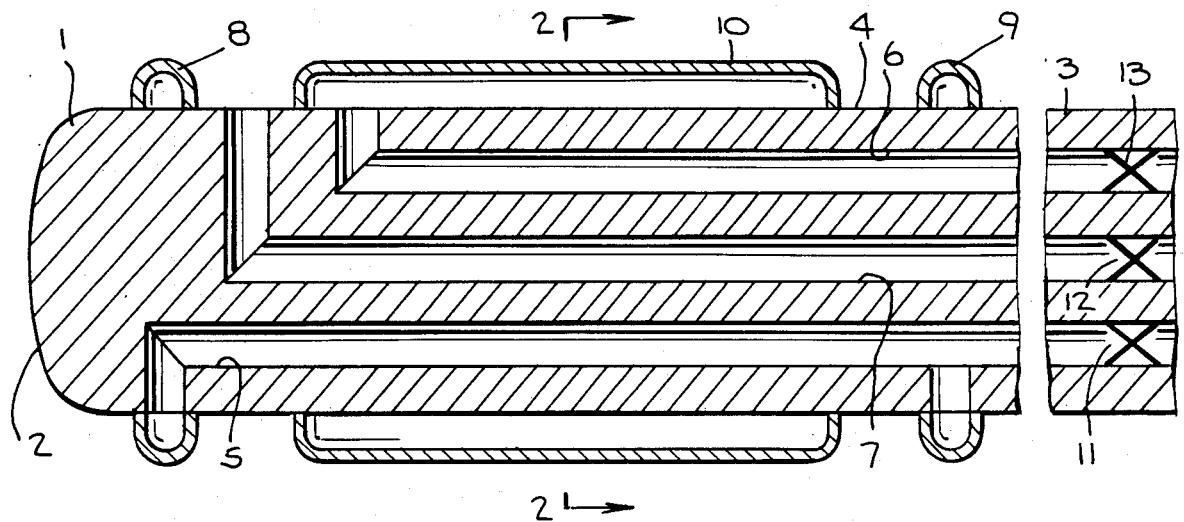
FIG. 1 is a schematic longitudinal sectional view of a catheter element which may be employed in this invention at the distal end of a main catheter body.
Figure 2:
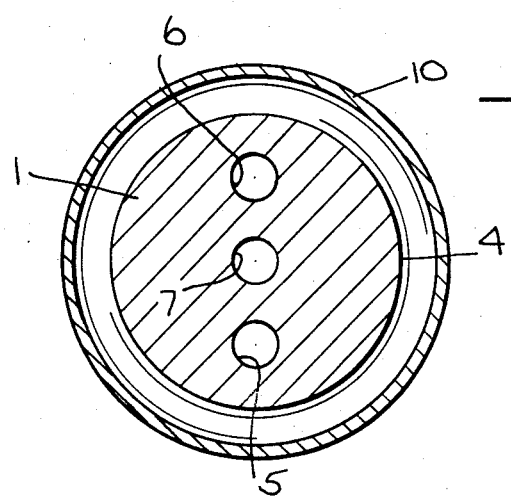
FIG. 2 is a cross section taken along the line 2—2 of FIG. 1.

FIGS. 1 and 2 illustrate the solubilizing fluid delivery, balloon carrying element of a catheter useful in the practice of this invention. In the embodiment illustrated it comprises a main catheter body generally designated as 1 with a distal end 2 and a proximate end 3 formed with a main catheter body wall 4. The main catheter body 1 is formed with three conduits; a ring balloon expansion conduit 5, a central balloon expansion conduit 6 and a fluid delivery conduit 7. The catheter body 1 carries two ring balloons 8 and 9 at either end, and an optional central balloon 10 disposed intermediate the spaced balloons. It also carries a third conduit 7 which exits through the catheter body. Conduits 5, 6 and 7 are fitted with appropriate valves 11, 12 and 13.

THE INVENTION

It has been found that catheters of the class described are useful for delivering heparin or other SMC growth regulators to the site of the angioplasty and depositing it in and about the site of the vascular wall damage to retard SMC growth.

The term 'heparin' as used herein refers to any of a variety of heparin products which inhibit SMC proliferation. Heparin from various sources is known to be heterogeneous. There are both anticoagulant and non-anticoagulant fractions. Each has varying degress of N- and O-sulfation and acetylation. Fractions with anticoagulant activity may contain as many as 20 saccharide moieties. It has been found that both anticoagulant and non-anticoagulant fractions manifest inhibition of SMC proliferation, and that heparin fractions or derivatives containing at least six saccharide monomers have this activity. Fractions and derivatives with varying degrees of sulfation manifest varying abilities to inhibit SMC proliferation. The active materials are described in detail in the Circulation Research publications cited above. All such fractions and derivatives are useful in the practice of this invention and are included within the term heparin.

Figure 3:
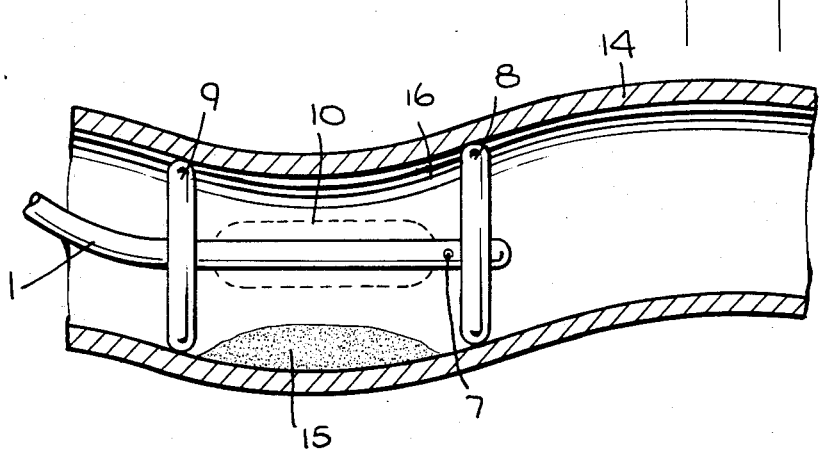
FIG. 3 is a view of the catheter element of FIG. 1 operatively positioned within a stenotic artery.

The operation of the catheter to form a chamber within the artery is schematically illustrated in FIG. 3.

In FIG. 3, 14 is the arterial wall of an artery constricted due to the presence of plaque body 15. The figures shows the main catheter body 1 held in place by the inflation of spaced balloons 8 and 9. The inflation of the balloons forms a chamber 16 in the artery and, as shown, surrounding the plaque. The catheter 1 is shown with the central balloon 10 in the deflated configuration. It also shows the delivery end of the third conduit 7.

In the practice of this invention, the two balloon catheter illustrated in the figures is employed following conventional angioplasty which removes at least a portion of the plaque. The angioplasty catheter is removed and the catheter 1 is inserted. The catheter 1 is guided by standard procedures which may include the use of a flexible probe, a guide wire and/or a fluoroscope to a position overlaying the original site of the plaque body 15 preferably, but not necessarily, in the position shown in FIG. 3 with the distal end balloon 8 just beyond the distal end of the original site and proximate end balloon 9 just ahead of the proximate end of the site. When the balloons 8 and 9 are inflated by forcing fluid such as isotonic saline through valve 11 and conduit 5, the catheter is held in place by the pressure of the balloons and a chamber 16 is formed surrounding the site. The closing of valve 11 will maintain the pressure in the conduit 5 and balloons 8 and 9 so that the catheter is held in place. The position of the catheter can be checked fluoroscopically or by passing a small amount of solubilizing liquid containing a dye into the chamber. If the position is not satisfactory the pressure can be released sufficiently to slightly deflate the ring balloons 8 and 9, the catheter moved in the appropriate direction, and the balloons reinflated.

Once the catheter is in place, the heparin is forced under pressure through the conduit 7 and the chamber 16 on and into the adjacent surfaces. Pressures of 200 to 1000 mm Hg are generally sufficient for this purpose although variations from this range are acceptable. The preferred range is 300 to 1000 mm Hg. The pressure at which the fluid is forced into the chamber may be generated by a pump upstream of valve 12. After the heparin is injected, the catheter is held in place for 5 to 60 seconds to hold the heparin in the chamber and provide time for it to stick to and penetrate the depths of the adjacent arterial tissue defined by the chamber in high concentration and not be prematurely washed away or diluted with the flowing blood. Balloons 8 and 9 are deflated, and the catheter removed.

Because of the large number of functional groups present, heparin is a highly charged molecule. When forced through the chamber 16 it enters the damaged wall and readily interacts with the surfaces of the various cells within the injured wall, as well as with the connective tissue between the cells. In effect it "sticks to" the injured site and inhibits, but does not completely stop the multiplying of SMC. Because heparin is 'sticky' it will stay in an effective position until the injury is healed.

The general process by which the injured artery repairs itself involves the bathing of the injured area with platelets and other cell growth promoters in the blood. The cells within the injured area of arterial wall continue to divide and multiply to generate new cellular tissue and repair the wound. When the growth reaches the appropriate level, the body's feedback mechanism signals the growth to stop. Restenosis occurs when the feed back mechanism is not functioning properly and the SMC continues to multiply in an uncontrolled manner in the damaged angioplasty site. The presence of the heparin appears in some manner to control the multiplication of the SMC cells so that they continue to multiply, but in a controlled manner until the regular control mechanism of the body takes over. The heparin affects only the deeper SMC cells and does not affect the surface endothelial cells.

An alternative procedure to the use of the two balloon catheter as described above is to use the three balloon catheter. In this method the catheter is inserted and placed over the plaque using the procedure described. The first step is to inflate the middle balloon, 10 to rupture the plaque. The balloon is deflated; after restoration of blood flow for a brief period, expansion of balloons 8 and 9 create a chamber around the angioplasty site. The heparin is then administered as described above. The chamber is held in place for 5 to 60 seconds so that the heparin can stick to and enter the adjacent surfaces, the balloons are deflated and then the catheter is removed.

The catheter body can be prepared from any of a number of readily available, non-toxic, flexible polymers including, for example, polyolefins, such as polyethylene or polypropylene, and polyvinyl halides, such as polyvinyl chloride or polyvinylidene chloride. The balloon can be fabricated from similar materials manufactured so as to be expansible under pressure and with sufficient elasticity to collapse when the pressure is released and negative pressure applied. The dimensions of the balloons will be such that they will reach the desired diameter at a pressure of from about 75 to 150 mm Hg and hold the dimensions even if the pressure is increased to as high as 5 or more atmospheres.

The absolute dimensions selected for the balloons will depend upon the diameter of the arteries involved. For example, the ring balloons may be from 2 to 5 mm in length and their expanded diameters will be approximately the same. The central balloon will be of the same diameter range as the end balloons, but the length will be from about 10 to 50 mm.

What is claimed is:

1. A method for inhibiting the proliferation of arterial smooth muscle cells following angioplasty which comprises the steps of:
    1. Conducting an angioplasty using a catheter with an expansible balloon to expand at least a portion of a plaque body and removing the catheter,
    2. Inserting into the artery a catheter comprising a main catheter body having means including two spaced balloon elements adapted to be positioned ajacent respective proximate and distal ends of the original site of the plaque body and to hold said main catheter body in place and expansible against the arterial walls for providing a chamber about said site, and means carried by said main catheter body for delivering heparin into said chamber,
    3. Inflating said two spaced balloon elements, to form a chamber at the site of the angioplasty,
    4. Delivering heparin into said chamber through said heparin delivering means under a pressure of 200 to 1000 mmHg at the site of the angioplasty whereby the heparin sticks to and penetrates the adjacent arterial tissue defined by the chamber,
    5. Deflating said two spaced balloon elements, and
    6. Removing the catheter from the artery.

2. A method as in claim 1 wherein the angioplasty is percutaneous transluminal coronary angioplasty.

3. A method for relieving an arterial constriction caused by a body of plaque and therafter inhibiting the proliferation of smooth muscle cells at the site of the plaque which comprises the steps of:
    1. Inserting into the artery a chateter comprising a main catheter body having means including two spaced balloon elements adapted to be positioned adjacent respective proximate and distal ends of the plaque body and expansible against the arterial walls for providing a chamber about said plaque body and to hold said main catheter body in place, means carried by said main catheter body for delivering heparin into said chamber, and means including a third expansible balloon element disposed intermediate said two spaced balloon elements,
2. Inflating said third balloon element against said plaque body to perform an angioplasty and to expand at least a portin of the plaque body,
3. Deflating said third balloon element,
4. Inflating said two spaced balloon elements to form a chamber at the site of the angioplasty,
5. Delivering heparin into said chamber through said heparin delivering means under a pressure of 200 to 1000 mmHg at the site of the angioplasty whereby the heparin sticks to and penetrates the adjacent arterial tissue defined by the chamber,
6. Deflating said two spaced balloon elements, and
7. Revmoving the catheter from the artery.

4. A method as in claim 2 wherein the angioplasty is percutaneous transluminal coronary angioplasty.

5. A method for inhibiting the proliferation of arterial smooth muscle cells following angioplasty which comprises the steps of:
 1. Conducting an angioplasty and,
 2. Depositing heparin under a pressure of 200 to 1000 mmHg at the site of the angioplasty utilizing heparin depositing means, whereby the heparin sticks to and penetrates the arterial tissue in and adjacent to the angioplasty site.

6. A method for inhibiting the proliferation of arterial smooth muscle cells following angioplasty which comprises the steps of:
 1. Conducting an angioplasty using a catheter with an expansible balloon to expand at least a portion of the plaque body thereby creating a lesion site, and
 2. Depositing heparin under a pressure of 200 to 1000 mmHg at the lesion site of the angioplasty utilizing heparin depositing means, whereby the heparin sticks to and penetrates the arterial tissue of the lesion site and adjacent thereto.

* * * * *